United States Patent [19]
Breton et al.

[11] Patent Number: 6,106,846
[45] Date of Patent: Aug. 22, 2000

[54] USE OF AT LEAST ONE THERMAL SPRING WATER FROM VICHY AS A SUBSTANCE P ANTAGONIST

[75] Inventors: Lionel Breton, Versailles; Jacques Leclaire, Massy; Olivier de Lacharriere, Paris, all of France

[73] Assignee: Société L'Oréal S.A., Paris, France

[21] Appl. No.: 08/716,535

[22] Filed: Sep. 19, 1996

[30] Foreign Application Priority Data

Sep. 19, 1995 [FR] France .................................. 95 10976

[51] Int. Cl.[7] ...................................................... A61K 7/48
[52] U.S. Cl. ............................ 424/401; 424/49; 424/70.1; 514/844; 514/846; 514/886; 514/887; 514/912; 514/937; 514/944
[58] Field of Search .................................... 424/401, 70.1, 424/49; 514/844, 846, 886, 887, 912, 937, 944

[56] References Cited

U.S. PATENT DOCUMENTS

| | | | |
|---|---|---|---|
| 5,679,360 | 10/1997 | De Lacharriere et al. | 424/401 |
| 5,690,946 | 11/1997 | Koulbanis et al. | 424/401 |
| 5,730,998 | 3/1998 | De Lacharriere et al. | 424/443 |
| 5,744,156 | 4/1998 | De Lacharriere et al. | 424/445 |

FOREIGN PATENT DOCUMENTS

| | | |
|---|---|---|
| 0533280 | 3/1993 | European Pat. Off. . |
| 0699432 | 3/1996 | European Pat. Off. . |
| 2546754 | 12/1984 | France . |
| 92/06666 | 4/1992 | WIPO . |
| 95/13793 | 5/1995 | WIPO . |

*Primary Examiner*—Jyothsna Venkat
*Attorney, Agent, or Firm*—Burns, Doane, Swecker & Mathis, L.L.P.

[57] ABSTRACT

The present invention relates to the use of at least one thermal spring water from the Vichy basin as substance P antagonist in a cosmetic composition or for the preparation of a pharmaceutical composition. The invention also relates to the use of at least one thermal spring water from the Vichy basin in a cosmetic composition or for the preparation of a pharmaceutical composition, more especially a dermatological composition, intended for treating disorders associated with excessive synthesis and/or release of substance P.

6 Claims, No Drawings

//  6,106,846

USE OF AT LEAST ONE THERMAL SPRING WATER FROM VICHY AS A SUBSTANCE P ANTAGONIST

BACKGROUND OF THE INVENTION

TECHNICAL FIELD OF THE INVENTION

The present invention relates to the use of at least one thermal spring water from the Vichy basin as substance P antagonist in a cosmetic composition or for the preparation of a pharmaceutical composition. The invention also relates to the use of at least one thermal spring water from the Vichy basin in a cosmetic composition or for the preparation of a pharmaceutical composition, more particularly a dermatological composition, intended for treating the disorders associated with excessive synthesis and/or release of substance P.

In mammals, there are polypeptides belonging to the family of the tachykinins which induce rapid contractions in the smooth muscle fibres. The compounds of this family include neurokinin β, neurokinin α and substance P.

Substance P is a polypeptide chemical component (an undecapeptide) which is produced and released by a nerve ending. The site of substance P is specific to the neurones, both in the central nervous system and in the peripheral organs. Therefore, a very large number of organs or tissues receive transmissions from neurones containing substance P; the organs or tissues involved are, in particular, the salivary glands, stomach, pancreas, the intestine (where the distribution of substance P is superposed on Auerbach's and Meissner's intrinsic nervous plexus), cardio-vascular system, thyroid gland, skin, iris and ciliary bodies, the bladder and of course the central and peripheral nervous systems.

Owing to the ubiquitous distribution of substance P, a very large number of disorders are associated with excessive synthesis and/or release of substance P.

Substance P participates, in particular, in the transmission of pain and in central nervous system disorders (for example anxiety, psychoses, neuropathies, neurodegenerative disorders of the type of Alzheimer's senile dementia, AIDS-related dementia, Parkinson's disease, Down's syndrome, Korsakoff's syndrome, multiple sclerosis, schizophrenia), in respiratory diseases (such as, for example, broncho-pneumonia) and inflammatory diseases (such as, for example, rheumatoid arthritis), in allergic syndromes (such as, for example, asthma, allergic rhinitis, allergic pharyngitis, urticaria, eczematous dermatitis), in gastro-intestinal diseases (such as, for example, ulcers, colitis, Crohn's disease), in skin disorders (such as, for example, psoriasis, pruriginous diseases, herpes, photodermatoses, atopic dermatitis, contact dermatitis, lichens, prurigo, pruritus, erythema, especially sun-related, insect stings), in fibroses and other collagen maturation disorders (such as, for example, scleroderma), in cardio-vascular disorders, vasospastic disorders (such as, for example, migraine, Reynaud's disease), in immunological disorders, in urinary tract disorders (such as, for example, incontinence, cystitis), in rheumatoid diseases, in certain dermatological diseases (such as eczema) and in ophthalmological complaints (such as, for example, conjunctivitis, uveitis, ocular pruritus, ocular pain, irritations).

The use of substance P antagonist is one of the therapeutic alternatives which are effective in all of the abovementioned complaints.

The term substance P antagonist is understood to refer to any compound which is capable of inhibiting, partially or even totally, the biological effect of substance P.

In particular, for a substance to be recognized as a substance P antagonist, it must induce a coherent pharmacological response (including or not including its binding to the substance P receptor), especially in one of the following tests:

the antagonist substance must decrease the extravasation of plasma through the vascular wall induced by capsaicin or by an antidromic nervous stimulation, or alternatively the antagonist substance must cause an inhibition of the smooth muscle contraction induced by the administration of substance P.

To date, substance P antagonists are used to treat the abovementioned disorders. To this end, reference may be made to the documents U.S. Pat. Nos. 4,472,305, 4,839,465, EP-A-101929, EP-A-333174, EP-A-336230, EP-A-394989, EP-A-443132, EP-A-498069, EP-A-515681, EP-A-517589, WO-A-92/22569, GB-A-2216529, EP-A-360390, EP-A-429366, EP-A-430771, EP-A-499313, EP-A-514273, EP-A-514274, EP-A-514275, EP-A-514276, EP-A-520555, EP-A-528495, EP-A-532456, EP-A-545478, EP-A-558156, WO-A-90/05525, WO-A-90/05729, WO-A-91/18878, WO-A-91/18899, WO-A-92/12151, WO-A-92/15585, WO-A-92/17449, WO-A-92/20676, WO-A-93/00330, WO-A-93/00331, WO-A-93/01159, WO-A-93/01169, WO-A-93/01170, WO-A-93/06099, WO-A-93/09116, EP-A-522808 and WO-A-93/01165.

The Applicant has recently discovered that a thermal spring water from the Vichy basin meets the criteria for a substance P antagonist and can therefore be used, in particular, for treating the abovementioned disorders.

The invention thus relates to the use of at least one thermal spring water from the Vichy basin as substance P antagonist in a cosmetic composition or for the preparation of a pharmaceutical composition.

The invention also relates to use of at least one thermal spring water from the Vichy basin in a cosmetic composition or for the preparation of a pharmaceutical composition which is intended for treating the disorders associated with excessive synthesis and/or release of substance P.

The spring water used in accordance with the invention may originate from the springs of Célestins, Chomel, Grande-Grille, Hôpital, Lucas and Parc.

Preferably, in accordance with the invention, water from the Lucas spring is used.

Examples have already been given in the text of disorders linked to excessive synthesis and/or release of substance P.

Thus, in accordance with one particular aspect, a subject of the invention is the use of at least one thermal spring water from the Vichy basin in a cosmetic composition or for the preparation of a pharmaceutical composition intended for treating disorders of the central nervous system, respiratory disorders, allergic syndromes, inflammation, pain, gastro-intestinal disorders, skin disorders, fibroses, collagen maturation disorders, cardio-vascular disorders, vasospastic disorders, immunological disorders and urinary tract disorders.

In the field of skin disorders, it is known that certain skins are more sensitive than others. However, the symptoms of sensitive skins have to date been poorly characterized and the problem of such skins was, as a consequence, poorly defined; no one knew exactly the process involved in the sensitivity of skin. Some thought that a sensitive skin was a skin which reacted to cosmetic products, others that such a skin reacted to a number of external factors not necessarily linked to cosmetic products. Sensitive skins were also classified along with allergic skins.

Tests have been developed to define sensitive skins, for example tests with lactic acid and with DMSO, which are known to be irritants: see, for example, the article by K. Lammintausta et al., Dermatoses, 1988, 36, pages 45–49; and the article by T. Agner and J. Serup, Clinical and Experimental Dermatology, 1989, 14, pages 214–217.

Owing to the lack of knowledge of the characteristics of sensitive skins, it was until now very difficult, or even impossible, to treat them. Indeed, they were treated indirectly, for example by limiting the use in cosmetic or dermatological compositions of products with an irritant nature such as surfactants, preservatives or fragrances, and the use of certain dermatological or cosmetic active agents.

Following numerous clinical tests, the Applicant has been able to determine the symptoms linked to sensitive skins. These symptoms are, in particular, subjective signs, which are essentially dysaesthetic sensations. Dysaesthetic sensations are understood to be more or less painful sensations felt in an area of skin, such as prickling, tingling, itching or pruritus, burning, hotness, discomfort, tightness, etc.

The Applicant has also been able to show that a sensitive skin is not an allergic skin. In effect, an allergic skin is a skin which reacts to an external agent, an allergen, which triggers an allergic reaction. This is an immunological process which occurs only when an allergen is present and which affects only sensitized subjects. The essential characteristic of sensitive skin on the other hand, according to the Applicant, is a mechanism of response to external factors which may affect any individual, even if individuals said to have sensitive skin react to these factors more quickly than other individuals. This mechanism is not immunological: it is aspecific.

The Applicant has found that sensitive skins can be divided into two major clinical forms: irritable and/or reactive skins, and intolerant skins.

An irritable and/or reactive skin is a skin which reacts by a pruritus, that is to say by itching, or by prickling, to various factors such as the environment, the emotions, food, the wind, abrasion, shaving, soap, surfactants, hard water with a high limestone concentration, changes in temperature, or wool. In general, these signs are associated with dry skin with or without sores, or with skin exhibiting an erythema.

Intolerant skin is skin which reacts by sensations of hotness, tightness, tingling and/or redness, to various factors such as the environment, the emotions, food and certain cosmetic products. In general, these signs are associated with hyperseborrhoeic skin or acneic skin with or without sores, and with an erythema.

"Sensitive" scalps have a clinical semiology which is more definite: the sensations of pruritus and/or prickling and/or hotness are essentially triggered by local factors such as abrasion, soap, surfactants, hard water with a high limestone concentration, shampoos or lotions. These sensations are also sometimes triggered by factors such as the environment, the emotions and/or food. Erythema and hyperseborrhoea of the scalp, and a dandruff condition, are frequently associated with the preceding signs.

Moreover, in certain anatomical regions such as those with considerable folds (inguinal, genital, axillary, popliteal, anal, inframammary and elbow-bend regions) and the feet, skin sensitivity here is manifested by pruriginous sensations and/or dysaesthetic sensations (hotness, prickling) which are linked, in particular, to perspiration, abrasion, wool, surfactants, certain cosmetic preparations, hard water with a high limestone concentration and/or changes in temperature.

To determine whether a skin is sensitive or not, the Applicant has likewise developed a test. Indeed, after having carried out a large number of tests with the aim of defining sensitive skin, a link was found to exist between persons with sensitive skin and those who reacted to topical application of capsaicin.

The test with capsaicin consists in applying, over approximately 4 $cm^2$ of skin, 0.05 ml of a cream containing 0.075% of capsaicin and in recording the appearance of subjective signs caused by this application, such as prickling, burning and itching. In subjects with sensitive skin, these signs appear between 3 and 20 minutes after the application and are followed by the appearance of an erythema which begins at the periphery of the area of application.

To date, capsaicin has been used as a medicament, in particular for treating the pains of shingles. Capsaicin causes a release of neuropeptides, and especially of tachykinins which originate from nerve endings of the epidermis and the dermis. The Applicant has found that the physiopathological mechanism common to all the states of sensitive skins was associated with a great capacity to release tachykinins and, more particularly, substance P in the skin. The dysaesthetic manifestations which are provoked by their release are termed "neurogenic".

No one had established a link between substance P and sensitive skin. The clinical signs of sensitive skin are essentially subjective: prickling, tingling, pruritus, tightness, hotness, and are sometimes associated with erythemas. These signs are caused by aspecific external factors. The symptoms appear essentially localized to the face, neck and scalp, but may also appear on all of the body.

Thus the Applicant discovered that one of the essential characteristics of sensitive skins is linked to the release of substance P and therefore that the use of substance P antagonists may make it possible to obtain a preventive and/or curative effect for sensitive skins.

To treat sensitive skins, therefore, the Applicant has envisaged using substance P antagonists. It has in fact been observed, surprisingly, that the incorporation of a substance P antagonist into a composition intended for topical use makes it possible to avoid irritation and/or dysaesthetic sensations and/or pruritus of the skin.

The invention therefore relates more particularly to the use of at least one thermal spring water from the Vichy basin in a cosmetic composition or for the preparation of a pharmaceutical composition intended for treating sensitive skins.

Another subject of the present invention is the use of at least one thermal spring water from the Vichy basin in a cosmetic composition or for the preparation of a pharmaceutical composition intended for preventing and/or combating skin irritations and/or sores and/or erythemas and/or sensations of hotness and/or of dysaesthesia and/or pruritus of the skin and/or mucosae.

According to the invention, the water can be used in a quantity representing from 0.1% to 60% of the total weight of the composition and preferably in a quantity representing from 1% to 30% of the total weight of the composition.

The thermal spring water from the Vichy basin can be used in a composition which is to be ingested, injected or applied to the skin (to any skin area of the body), hair, nails or mucosae (buccal, jugal, gingival, genital, anal, conjunctive). Depending on the method of administration, this composition can be in any of the normally used pharmaceutical forms.

For topical application to the skin, the composition can take the form, in particular, of an aqueous solution or oily suspension or dispersion of the lotion or serum type, of emulsions with a liquid or semi-liquid consistency of the milk type, which are obtained by dispersion of a fatty phase in an aqueous phase (O/W) or vice versa (W/O), or of suspensions or emulsions with a soft consistency, of the cream, aqueous gel or nonaqueous gel type, or else of microcapsules or of microparticles, or of vesicle dispersions of ionic and/or nonionic type. These compositions are prepared according to the usual methods.

They may also be used for hair in the form of aqueous, alcoholic or aqueous-alcoholic solutions, or in the form of creams, gels, emulsions, mousses, or else in the form of aerosol compositions also containing a pressurized propellant.

For injection, the composition can be in the form of an aqueous lotion, an oily suspension or in the form of a serum. For the eyes, it can be in the form of drops, and for ingestion it can be in the form of capsules, granules, syrups or tablets.

The quantities of the various constituents of the compositions according to the invention are those conventionally employed in the fields under consideration.

These compositions constitute, in particular, cleansing creams, protection creams, treatment creams or care creams for the face, hands, feet, major anatomical folds or body (for example day creams, night creams, make-up removing creams, foundation creams, sun protection creams), liquid foundations, make-up removing milks, body milks for protection or care, sun protection milks, lotions, gels or mousses for skin care, such as cleansing lotions, sun protection lotions, artificial tanning lotions, bath compositions, deodorant compositions including a bactericidal agent, after-shave gels or lotions, depilatory creams, compositions to counter insect stings, pain relief compositions, compositions for treating certain skin diseases such as eczema, rosacea, psoriasis, lichens and severe pruritus.

The compositions can also consist of solid preparations constituting soaps or cleansing bars.

The compositions may also be packaged in the form of an aerosol composition also including a pressurized propellant.

The thermal spring water from the Vichy basin which is used in accordance with the invention can also be incorporated into various compositions for hair care, and especially shampoos, setting lotions, treatment lotions, styling creams or gels, dyeing compositions (especially oxidation dyes), possibly in the form of colouring shampoos, restructuring lotions for the hair, perming compositions (especially compositions for the first stage of a perm), lotions or gels to counter hair loss, antiparasitic shampoos, etc.

The compositions can also be for bucco-dental use, for example a toothpaste. In this case, the compositions can comprise adjuvants and additives which are customary for compositions for buccal use, and especially surfactants, thickeners, humectants, polishing agents such as silica, various active ingredients such as fluorides, especially sodium fluoride, and, optionally, sweeteners such as sodium saccharinate.

When the composition is an emulsion, the proportion of the fatty phase may range from 5% to 80% by weight, and preferably from 5% to 50% by weight, relative to the total weight of the composition. The oils, waxes, emulsifiers and co-emulsifiers which are used in the composition in emulsion form are chosen from those which are conventionally used in the cosmetic field. The emulsifier and the co-emulsifier are present in the composition in a proportion ranging from 0.3% to 30% by weight, and preferably from 0.5 to 20% by weight, relative to the total weight of the composition. The emulsion may additionally contain lipid vesicles.

When the composition is an oily gel or a solution, the fatty phase may represent more than 90% of the total weight of the composition.

As is known, the cosmetic composition may also contain adjuvants which are customary in the cosmetic field, such as hydrophilic or lipophilic gelling agents, hydrophilic or lipophilic additives, preservatives, antioxidants, solvents, fragrances, fillers, screening agents, odour absorbers and colorants. The quantities of these various adjuvants are those which are conventionally used in the cosmetic field, and are for example from 0.01% to 10% of the total weight of the composition. These adjuvants, depending on their type, may be introduced into the fatty phase, into the aqueous phase and/or into the lipid spherules.

As oils or waxes which can be used in the invention mention may be made of mineral oils (liquid petroleum oil), vegetable oils (the liquid fraction of shea butter, sunflower oil), animal oils (perhydrosqualene), synthetic oils (purcellin oil), silicone oils or waxes (cyclomethicone) and fluorinated oils (perfluoropolyethers), beeswax, carnauba wax or paraffin wax. To these oils it is possible to add fatty alcohols and fatty acids (stearic acid).

As emulsifiers which can be used in the invention mention may be made, for example, of glycerol stearate, polysorbate 60 and the PEG-6/PEG-32/glycol stearate mixture sold under the name Tefose$^R$ 63 by Gattefosse.

As solvents which can be used in the invention mention may be made of lower alcohols, especially ethanol and isopropanol, and propylene glycol.

As hydrophilic gelling agents which can be used in the invention mention may be made of carboxyvinyl polymers (Carbomer), acrylic copolymers such as acrylate/alkyl acrylate copolymers, polyacrylamides, polysaccharides such as hydroxypropylcellulose, natural gums and clays and, as lipophilic gelling agents, mention may be made of modified clays such as Bentones, metal salts of fatty acids, such as aluminium stearates, and hydrophobic silica, ethylcellulose and polyethylene.

The composition may contain other hydrophilic active agents, such as proteins or protein hydrolysates, amino acids, polyols, urea, allantoin, sugars and sugar derivatives, water-soluble vitamins, plant extracts and hydroxy acids.

As lipophilic active agents it is possible to use retinol (vitamin A) and its derivatives, tocopherol (vitamin E) and its derivatives, essential fatty acids, ceramides, essential oils, salicylic acid and its derivatives.

According to the invention it is possible, inter alia, to combine at least one thermal spring water from the Vichy basin with other active agents which are intended, in particular, for the prevention and/or treatment of skin disorders.

Examples which may be mentioned among these active agents are:
  agents which modulate differentiation and/or proliferation and/or skin pigmentation, such as retinoic acid and its isomers, retinol and its esters, vitamin D and its derivatives, oestrogens such as oestradiol, kojic acid or hydroquinone;
  antibacterials such as clindamycin phosphate, erythromycin or antibiotics of the tetracyclin class;
  antiparasitics, especially metronidazole, crotamiton or pyrethrinoids;
  antifungals, especially compounds belonging to the class of the imidazoles, such as econazole, ketoconazole or miconazole or their salts, polyene compounds, such as amphotericin B, compounds of the allylamine family, such as terbinafine, or alternatively octopirox;
  antiviral agents such as acyclovir;
  steroidal anti-inflammatory agents such as hydrocortisone, betamethasone valerate or clobetasol propionate, or nonsteroidal anti-inflammatory agents such as ibuprofen and its salts, diclofenac and its salts, acetylsalicylic acid, acetaminophen or glycyrrhetinic acid;

anaesthetic agents, such as lidocaine hydrochloride and its derivatives;

antipruriginous agents such as thenaldine, trimeprazine or cyproheptadine;

keratolytic agents such as alpha- and beta-hydroxycarboxylic or beta-ketocarboxylic acids, their salts, amides or esters, and, more particularly, hydroxy acids such as glycolic acid, lactic acid, salicylic acid, citric acid and, generally, the fruit acids, and n-octanoyl-5-salicylic acid;

free-radical scavengers, such as alpha-tocopherol or its esters, superoxide dismutases, certain metal chelating agents or ascorbic acid and its esters;

antiseborrhoeic agents such as progesterone;

antidandruff agents such as octopirox or zinc pyrithione;

anti-acne agents, such as retinoic acid or benzoyl peroxide.

Thus, according to a particular embodiment, the invention relates to the use of at least one thermal spring water from the Vichy basin in a composition comprising at least one agent chosen from antibacterial agents, antiparasitic agents, antifungals, antiviral agents, anti-inflammatory agents, anti-pruriginous agents, anaesthetics, keratolytic agents, free-radical scavengers, antiseborrhoeic agents, anti-dandruff agents, anti-acne agents and/or agents modulating differentiation and/or proliferation and/or skin pigmentation.

A further subject of the present invention is a method of cosmetic treatment with the aim of reducing the pain linked to excessive synthesis and/or liberation of substance P, characterized in that a composition comprising a thermal spring water from the Vichy basin is applied to the skin, hair and/or mucosae.

The cosmetic treatment method of the invention can be employed, in particular, by applying the hygienic or cosmetic compositions as defined above in accordance with the normal technique for use of these compositions. For example: application of creams, gels, sera, lotions, make-up removing milks or sun protection compositions to the skin or dry hair, application of a hair lotion to wet hair, of shampoos, or else application of dentifrice to the gums.

The following compositions and examples illustrate the invention without limiting it in any way. In the compositions, the proportions indicated are percentages by weight.

EXAMPLE 1

Pharmacological Activity of One of the Thermal Spring Waters From the Vichy Basin Functional Test in Vivo on a Model of Neurogenic Inflammation A functional test in vivo is carried out on a model of neurogenic inflammation in order to demonstrate the substance P antagonist nature of one of the spring waters from the Vichy basin (water from the Lucas spring).

The in vivo experiments are carried out in accordance with the method described by Xu X. J. and colleagues (Neurosciences, 1991, 42, 731–737).

The test consists in bringing about neurogenic inflammation by antidromic stimulation of the saphenous nerve in the anaesthetized animal. This nerve innervates the skin areas of the posterior paws. The stimulation brings about the release of substance P from the nerve endings, which is partly responsible for the neurogenic inflammation. The neurogenic inflammation is quantified by measuring the tissue permeability to Evans blue, a marker of the tissue extravasation of blood albumin which takes place in the course of the inflammation. This reference model is used for researching substance P antagonists in vivo.

Eau de Vichy from the Lucas spring, administered in pure form, brings about a statistically significant reduction of 40% in the neurogenic inflammation.

Under the same conditions, a water originating from La Roche Posay has no statistically significant anti-inflammatory effect.

EXAMPLE 2

Formulation examples illustrating the invention. These compositions were obtained simply by mixing the various components.

| Composition 1: Make-up removal lotion for the face | | |
|---|---|---|
| Eau du bassin de Vichy [Vichy basin water] | | 10.00 |
| Antioxidant | | 0.05 |
| Isopropanol | | 40.00 |
| Preservative | | 0.30 |
| Water | q.s. for | 100% |
| Composition 2: Face care gel | | |
| Eau du bassin de Vichy | | 20.00 |
| Hydroxypropylcellulose (Klucel H sold by Hercules) | | 1.00 |
| Antioxidant | | 0.05 |
| Isopropanol | | 40.00 |
| Preservative | | 0.30 |
| Water | q.s. for | 100% |
| Composition 3: Face care cream (oil-in-water emulsion) | | |
| Eau du bassin de Vichy | | 10.00 |
| Glycerol stearate | | 2.00 |
| Polysorbate 60 (Tween 60 sold by ICI) | | 1.00 |
| Stearic acid | | 1.40 |
| Triethanolamine | | 0.70 |
| Carbomer | | 0.40 |
| Liquid fraction of shea butter | | 12.00 |
| Perhydrosqualene | | 12.00 |
| Antioxidant | | 0.05 |
| Fragrance | | 0.5 |
| Preservative | | 0.30 |
| Water | q.s. for | 100% |
| Composition 4: Shampoo | | |
| Eau du bassin de Vichy | | 5.00 |
| Hydroxypropylcellulose (Klucel H sold by Hercules) | | 1.00 |
| Fragrance | | 0.50 |
| Preservative | | 0.30 |
| Water | q.s. for | 100% |
| Composition 5: Pain relief gel | | |
| Eau du bassin de Vichy | | 30.00 |
| Hydroxypropylcellulose (Klucel H sold by Hercules) | | 1.00 |
| Antioxidant | | 0.05 |
| Lidocaine hydrochloride | | 2.00 |
| Isopropanol | | 40.00 |
| Preservative | | 0.30 |
| Water | q.s. for | 100% |

| Composition 6: Care cream for solar erythema (oil-in-water emulsion) | |
|---|---|
| Eau du bassin de Vichy | 30.00 |
| Glycerol stearate | 2.00 |
| Polysorbate 60 (Tween 60 sold by ICI) | 1.00 |
| Stearic acid | 1.40 |
| Glycyrrhetinic acid | 2.00 |
| Triethanolamine | 0.70 |
| Carbomer | 0.40 |
| Liquid fraction of shea butter | 12.00 |
| Sunflower oil | 10.00 |
| Antioxidant | 0.05 |
| Fragrance | 0.5 |
| Preservative | 0.30 |
| Water q.s. for | 100% |

Composition 7: O/W emulsion intended for facial skin treatment

Fatty phase:

| | |
|---|---|
| Apricot kernel oil (triglycerides of oleic-linoleic acids) | 14.5% |
| Liquid fraction of shea butter (triglycerides of palmitic/stearic/ oleic/linoleic acid) | 7.0% |
| Propyl parahydroxybenzoate (preservative) | 0.1% |
| Fatty alcohol mixture (stearyl alcohol, arachidyl alcohol, behenyl alcohol) | 1.0% |
| Sorbitan monostearate (Span 60 from ICI) | 2.5% |
| Mixture of cetylstearyl 2-hexanoate and isopropyl myristate (purcellin oil) | 2.0% |

Aqueous phase:

| | |
|---|---|
| Preservatives | 0.5% |
| Disodium salt of ethylene diamine tetraacetic acid 2H$_2$O (complexing agent) | 0.05% |
| Neutralizing agent | 0.5% |
| Gelling agent | 0.7% |
| Glycerol | 5.0% |
| Ethoxylated sorbitan monostearate (20 EO) (Tween 60 from ICI) (surfactant) | 2.5% |
| n-Octanoyl-5-salicylic acid | 1% |
| Eaux du bassin de Vichy | 62.65% |
| Demineralized or deionized water q.s. for | 100% |

What is claimed is:

1. A method of treating a condition associated with neurogenic inflammation comprising topically applying an effective amount of a composition comprising an effective amount of at least one thermal spring water obtained from the Vichy basin.

2. The method of claim 1 wherein said composition is topically applied.

3. A method according to claim 1 wherein said water is contained in an amount ranging from 0.1% to 60% relative to the total weight of the composition.

4. The method according to claim 1 wherein the amount of said water ranges from 1% to 30% relative to the total weight of the composition.

5. The method according to claim 1 wherein said at least thermal spring water originates from the springs of Célestins, Chomel, Grand-Grille, Hôpital, Lucas or Parc.

6. The method according to claim 5 wherein said at least one thermal spring water is water obtained from the Lucas spring.

* * * * *